(12) United States Patent
Bhagat et al.

(10) Patent No.: US 10,639,126 B2
(45) Date of Patent: *May 5, 2020

(54) INSTRUMENT FIXATION DEVICE FOR DEPTH AND ANGLE FIXATION

(71) Applicant: COVIDIEN LP, Mansfield, MA (US)

(72) Inventors: Simranjeet Bhagat, Punjab (IN); Jeetendra Bharadwaj, Superior, CO (US)

(73) Assignee: COVIDIEN LP, Mansfield, MA (US)

( * ) Notice: Subject to any disclaimer, the term of this patent is extended or adjusted under 35 U.S.C. 154(b) by 363 days.

This patent is subject to a terminal disclaimer.

(21) Appl. No.: 15/482,132

(22) Filed: Apr. 7, 2017

(65) Prior Publication Data

US 2017/0209233 A1 Jul. 27, 2017

Related U.S. Application Data

(63) Continuation of application No. 14/326,762, filed on Jul. 9, 2014, now Pat. No. 9,629,659.

(51) Int. Cl.

| | |
|---|---|
| *A61B 90/50* | (2016.01) |
| *A61B 17/34* | (2006.01) |
| *A61B 90/53* | (2016.01) |
| *F16C 11/10* | (2006.01) |
| *A61B 17/00* | (2006.01) |

(Continued)

(52) U.S. Cl.
CPC .......... *A61B 90/50* (2016.02); *A61B 17/3403* (2013.01); *A61B 17/3423* (2013.01); *A61B 17/3462* (2013.01); *A61B 17/3494* (2013.01); *A61B 90/53* (2016.02); *F16C 11/106* (2013.01); *A61B 2017/00477* (2013.01); *A61B 2017/00889* (2013.01); *A61B 2017/00946* (2013.01); *A61B 2017/347* (2013.01); *A61B 2017/3407* (2013.01); *A61B 2017/3492* (2013.01); *A61B 2034/2051* (2016.02);

(Continued)

(58) Field of Classification Search
None
See application file for complete search history.

(56) References Cited

U.S. PATENT DOCUMENTS

| | | |
|---|---|---|
| 5,020,933 A | 6/1991 | Salvestro et al. |
| 5,308,352 A | 5/1994 | Koutrouvelis |

(Continued)

FOREIGN PATENT DOCUMENTS

WO 2010017641 A1 2/2010

OTHER PUBLICATIONS

European Office Action dated Jul. 5, 2017, issued in EP Application No. 15 175 746.

(Continued)

*Primary Examiner* — Shaun L David

(57) ABSTRACT

An instrument fixation device includes a retaining ring, a ball joint disposed within and movable relative to the retaining ring, and a locking mechanism. The ball joint defines a channel configured to receive an instrument therethrough. The locking mechanism includes a locking sleeve and a lock. The locking sleeve is at least partially disposed within the retaining ring and engages the outer surface of the ball joint. When the locking mechanism is in an unlocked position, the ball joint is free to move within the retaining ring and when the locking mechanism is in a first locked position, the locking sleeve engages the outer surface of the ball joint to fix the ball joint relative to the retaining ring.

19 Claims, 7 Drawing Sheets

(51) Int. Cl.
*A61B 90/00* (2016.01)
*A61B 34/20* (2016.01)

(52) U.S. Cl.
CPC ... *A61B 2090/062* (2016.02); *A61B 2090/067* (2016.02); *A61B 2090/0811* (2016.02)

(56) References Cited

U.S. PATENT DOCUMENTS

| | | |
|---|---|---|
| 5,662,613 A | 9/1997 | Astarita |
| 6,086,603 A | 7/2000 | Termin et al. |
| 6,238,124 B1 | 5/2001 | Merlo |
| 6,290,196 B1 | 9/2001 | Mayenberger |
| 8,216,211 B2 | 7/2012 | Mathis et al. |
| 9,629,659 B2 | 4/2017 | Bhagat et al. |
| 2002/0042595 A1 | 4/2002 | Palmer et al. |
| 2003/0028179 A1 | 2/2003 | Piskun |
| 2004/0068232 A1 | 4/2004 | Hart et al. |
| 2004/0092965 A1 | 5/2004 | Parihar |
| 2009/0030443 A1 | 1/2009 | Buser et al. |
| 2009/0036745 A1 | 2/2009 | Bonadio et al. |
| 2009/0227843 A1 | 9/2009 | Smith et al. |
| 2010/0042111 A1 | 2/2010 | Qureshi et al. |
| 2010/0048997 A1 | 2/2010 | Okada |
| 2010/0057010 A1 | 3/2010 | Goransson |
| 2010/0081882 A1 | 4/2010 | Hess et al. |
| 2012/0296281 A1 | 11/2012 | Jaspers et al. |
| 2013/0072759 A1 | 3/2013 | Li et al. |
| 2013/0096505 A1 | 4/2013 | Urmey |
| 2014/0275801 A1 | 9/2014 | Menchaca et al. |

OTHER PUBLICATIONS

European Search Report dated Nov. 23, 2015, issued in EP Application No. 15175746.

INSTRUMENT FIXATION DEVICE FOR DEPTH AND ANGLE FIXATION

CROSS-REFERENCE TO RELATED APPLICATION

This application is a continuation of U.S. patent application Ser. No. 14/326,762, filed Jul. 9, 2014, now U.S. Pat. No. 9,629,659, the entire contents of which are incorporated herein by reference.

BACKGROUND

1. Technical Field

The present disclosure relates to surgery and, more specifically, to instrument fixation devices to fix the depth and angle of an instrument passed through a channel of the device.

2. Discussion of Related Art

This present disclosure relates to devices and methods for performing surgical procedures including minimally invasive surgical procedures (e.g., laparoscopic or endoscopic surgical procedures). More particularly, the present disclosure relates to devices and methods for fixing the position of an instrument during a surgical procedure.

Minimally invasive surgical instruments and methods have been developed for treating tissue that are less intrusive and less traumatic. For example, with one known technique, the surgeon makes a few small incisions in the abdomen and inserts one or more elongated surgical instruments, e.g., electrosurgical instruments, forceps, scissors, clip appliers, staplers, etc., into the incision and carefully manipulates the instruments while viewing the operating area through an endoscope or laparoscope.

Minimally invasive surgical procedures require a surgeon to insert different instruments through a surgical site (e.g., an incision or natural orifice) to perform the surgical procedure. During insertion and operation of the instruments, it may be necessary to hold a surgical instrument steady within the surgical site. Traditionally, a surgeon would use one hand to hold the instrument in place within the surgical site to fix the depth and angle of the surgical instrument within the surgical site. When additional instruments are used during a surgical procedure, two or more people may be required to complete the surgical procedure to steady the instruments. Surgeries that require two people are generally more expensive and the potential for error is increased. Hence, it is desirable to modify a procedure so that it may be performed with one or two hands, if possible.

Accordingly, there is a need for a device for use during a surgical procedure to fix the angle and depth of a surgical instrument within a surgical site that would facilitate operation of multiple surgical instruments by a single practitioner.

SUMMARY

In an aspect of the present disclosure, an instrument fixation device includes a retaining ring, a ball joint, and a locking mechanism. The ball joint has an outer surface that is disposed within and movable relative to the retaining ring. The ball joint defines a channel therethrough. The locking mechanism includes a locking sleeve and a lock. The locking sleeve is partially disposed within the retaining ring and is engagable with the outer surface of the ball joint. The lock includes an engagement portion configured to engage the outer surface of the ball joint. In an unlocked position of the locking mechanism, the ball joint is free to move within the retaining ring. In a first locked position of the locking mechanism, the locking sleeve engages the outer surface of the ball joint fixing the ball joint relative to the retaining ring.

In some aspects, the instrument fixation device includes a position sensor that is configured to provide an indication of the location of the device relative to a surgical site. The position sensor may be disposed on or in the retaining ring. Additionally or alternatively, the instrument fixation device includes an angular sensor that is configured to provide an indication of the orientation of the ball joint relative to the retaining ring. The position sensor may be disposed on or in the ball joint or the retaining ring.

In certain aspects, the instrument fixation device includes a malleable pad fixed to a bottom surface of the retaining ring. The malleable pad may include a plurality of wings extending radially away from the retaining ring. One or more of the plurality of wings may define a suture hole configured to receive a suture that secures the device to a patient. The malleable pad may have anti-microbial properties.

In aspects, the ball joint has an unsecured configuration such that a surgical instrument is free to slide and rotate within the channel and a secured configuration such that the surgical instrument is fixed within the channel relative to the ball joint. The ball joint may include two or more lobes. The channel may be a deformable channel such that in the unsecured configuration, the deformable channel is undeformed and in the secured configuration, the deformable channel is deformed. The locking mechanism may include a second locked position such that the locking sleeve engages the outer surface of the ball joint to fix the ball joint relative to the retaining ring and to deform the deformable channel.

In some aspects, the ball joint is movable in six degrees of freedom relative to the retaining ring. The lock may provide tactile feedback to a clinician when the locking mechanism transitions from the unlocked position to the first locked position. The lock may engage the locking sleeve to engage the locking sleeve with the ball joint.

In another aspect of the present disclosure, a surgical navigation system includes a surgical instrument and an instrument fixation device. The instrument fixation device may be any of the instrument fixation devices disclosed herein.

In some aspects, the instrument fixation device includes an instrument sensor that is configured to provide an indication of a length of the surgical instrument extending through the channel and into a surgical site. The surgical instrument may have a distal end portion that extends from the channel of the ball joint and into the surgical site. The instrument fixation device may include a position sensor that is configured to provide an indication of the position of the instrument fixation device. The system may be configured to determine a length of the surgical instrument extending into a surgical site from the length of the instrument that extends from the channel and the position of the instrument fixation device.

In still other aspects of the present disclosure, a method for positioning a surgical instrument within a surgical site includes securing an instrument fixation device to a patient over a surgical site, inserting a length of a surgical instrument through a channel of the instrument fixation device and into the surgical site, determining the length of the surgical instrument within the surgical site, locking a ball joint of the instrument fixation device relative to a retaining ring with a locking mechanism of the instrument fixation device, and securing the surgical instrument relative to the ball joint. The instrument fixation device and the surgical instrument may be any of the instrument fixation devices and surgical instruments disclosed herein.

In aspects, locking the ball joint relative to the retaining ring includes moving a lock of the locking mechanism to a first locked position. In some aspects, securing the surgical instrument relative to the ball joint includes moving a lock of the locking mechanism to a second locked position.

The method may include providing an indication to a clinician when the instrument fixation device is positioned about the surgical site before securing the instrument fixation device to the patient. The instrument fixation device may include a position sensor that provides an indication of the position of the instrument fixation device relative to a surgical site of a patient.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Figure 1:
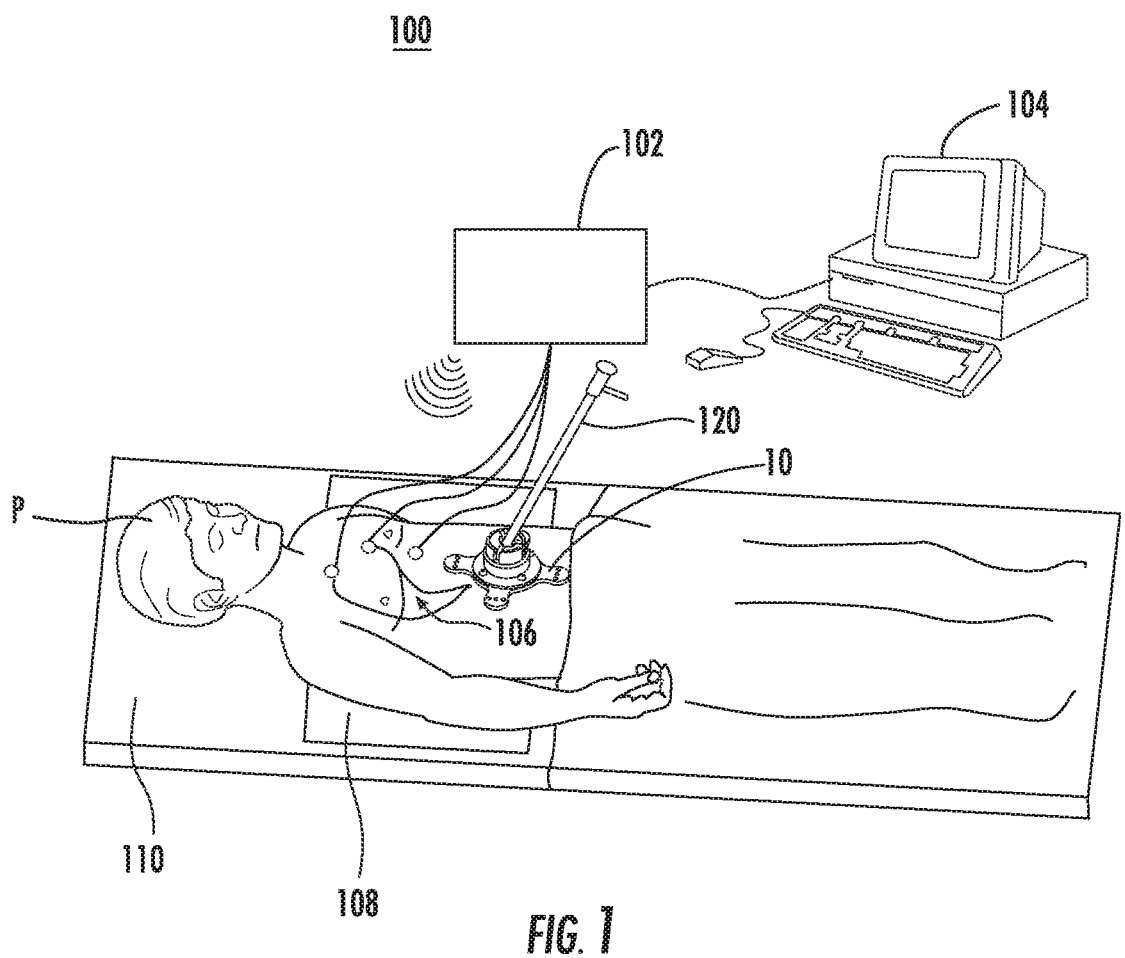
FIG. 1 is a perspective view of a surgical positioning system connected to a patient, in accordance with one illustrative embodiment of the present disclosure, the system including a tracking module, a computer, an instrument, and an instrument securement device.

In accordance with the present disclosure, a surgical positioning system includes an instrument fixation device that is detectable by the surgical position system such that the position of the instrument fixation device within a surgical environment is known by the surgical positioning system. The surgical positioning system may include surgical instruments that are positionable relative to the instrument fixation device such that the instrument fixation device fixes the surgical instrument within the surgical site. The surgical positioning system may determine the position of the surgical instrument within the surgical site based on the length of a surgical instrument inserted through the instrument fixation device, the angle of the surgical instrument relative to the surgical positioning system, and the position of the instrument fixation device.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, a surgical positioning system 100 is provided in accordance with the present disclosure and includes an instrument fixation device 10, a tracking module 102, reference sensors 106, a reference mat 108, and a surgical instrument 120. The surgical positioning system 100 is configured to determine the position of the surgical instrument 120 within a surgical site of the patient P.

The tracking module 102 may utilize a Six Degrees Of Freedom (SDOF) electromagnetic position measuring system according to the teachings of U.S. Pat. No. 6,188,355 and published PCT Application Nos. WO 00/10456 and WO 01/67035, which are incorporated herein by reference. The reference mat 108 may be an electromagnetic filed transmitter positioned beneath the patient "P." The reference sensors 106 are placed on the patient "P" such that their location within the electromagnetic field generated by the reference mat 108 can be detected. The location of each sensor 106 is determined in and sent to tracking module 102. One of skill in the art will recognize that the tracking module 102 may be incorporated into a computer 104 as a software component and need not be a separate component as depicted in FIG. 1.

The instrument fixation device 10 is configured to secure to the skin of the patient P about a surgical site and provide an indication of its position to the tracking module 102. The surgical site may be a natural orifice or an incision in the skin of a patient. The surgical positioning system 100 may use the position of the instrument fixation device 10 to determine the position of the surgical instrument 120 within the surgical site as detailed below.

Figure 2:
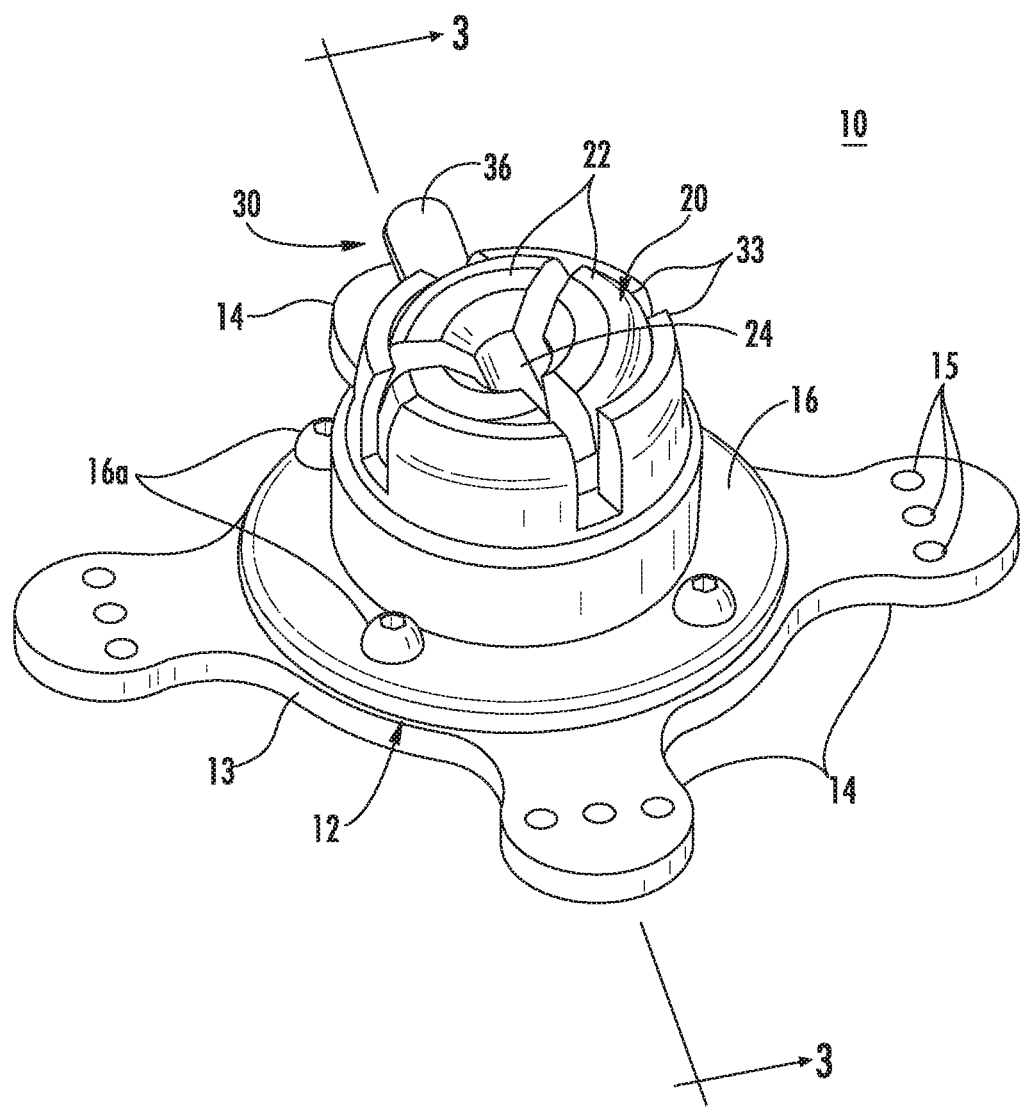
FIG. 2 is a perspective view of the instrument securement device of FIG. 1.
Figure 3:
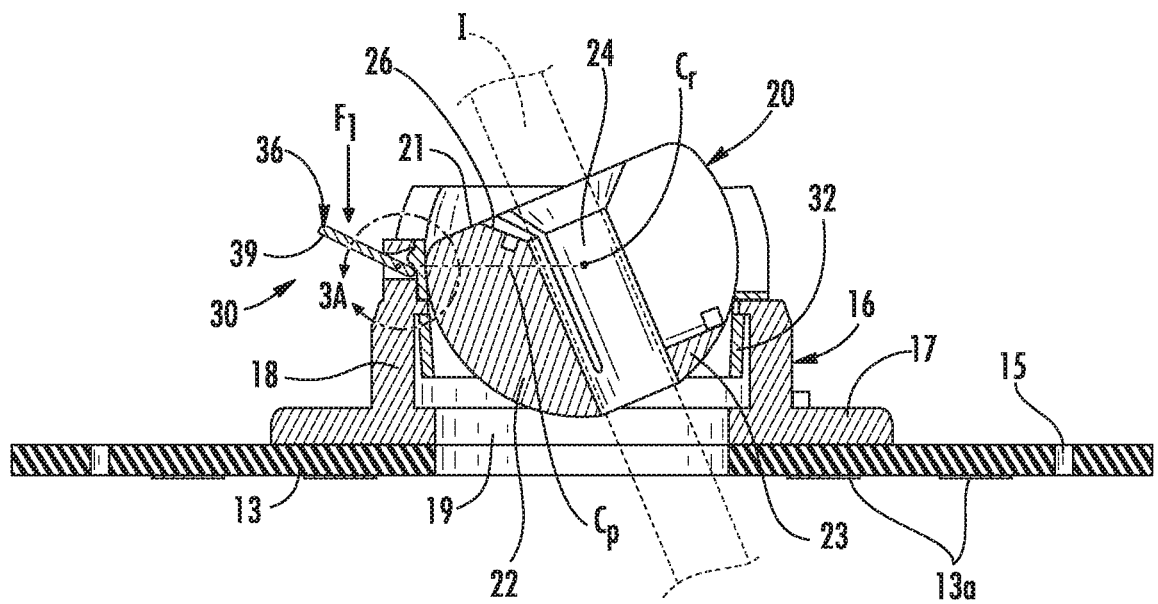
FIG. 3 is a side, cross-sectional view taken along the line 3-3 of FIG. 2 illustrating the locking mechanism in an unlocked position and a channel of the ball joint in an unsecured configuration.

With reference to FIGS. 2 and 3, the instrument fixation device 10 includes a base 12, a ball joint 20, and a locking mechanism 30. The base 12 includes a malleable pad 13 and a retaining ring 16. The malleable pad 13 may be integrally formed with the retaining ring 16. Alternatively or additionally, the malleable pad 13 may be secured to the retaining ring 16 with adhesive or fasteners 16a. The malleable pad 13 includes two or more wings 14 configured to secure the device 10 to the skin of the patient P. The malleable pad 13 may be constructed of a soft material. The malleable pad 13 may have an anti-microbial coating or be made entirely of an anti-microbial material to reduce the risk of bacterial infection at the surgical site. One or more of the wings 14 may define a suture hole 15 through the upper and lower surface thereof such that a clinician may pass a suture (not shown) through the suture hole 15 to secure the instrument fixation device 10 to the patient. Alternatively or additionally, the lower surface of the malleable pad 13 may include an adhesive 13a to secure the instrument fixation device 10 to the patient.

The ball joint 20 is disposed within a through passage 19 defined by the retaining ring 16. The ball joint 20 is substantially spherical in shape and may include a flattened upper surface 21. The ball joint 20 is configured to move within the retaining ring 16 and may be movable in SDOF relative to the retaining ring 16. The ball joint 20 defines a through channel 24 and includes two or more lobes 22 and a lower ring 23. The lobes 22 are integrally formed with the lower ring 23 and positioned radially about the channel 24. The channel 24 is configured to receive an instrument I (e.g., instrument 120). The flattened upper surface 21 may define a depression 26 about the channel 24 to guide the instrument "I" into the channel 24.

Figure 3A:
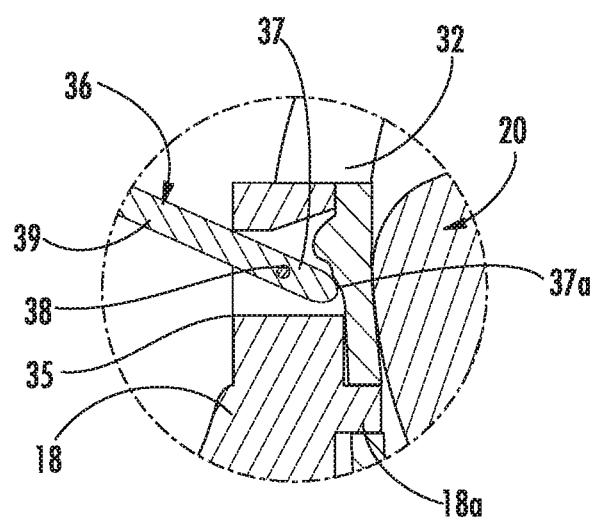
FIG. 3A is an enlarged view of the indicated area of detail of FIG. 3.

With particular reference to FIGS. 3 and 3A, the retaining ring 16 includes a base flange 17 and a ring portion 18. The retaining ring 16 and the malleable pad 13 define the through passage 19 substantially orthogonal to the base flange 17 and the malleable pad 13 to provide access to the surgical site through the instrument fixation device 10. The ring portion 18 may include a retention finger 18a extending towards the through passage 19 adjacent an upper surface thereof. The retention finger 18a is configured to secure the ball joint 16 and the locking mechanism 30 to the base 12.

The locking mechanism 30 includes a locking sleeve 32 and a lock 36. The locking sleeve 32 is disposed within the ring portion 18 of the retaining ring 16 and is secured by the retention finger 18a. A portion of the ring portion 18 includes a lock mount 35. The locking sleeve 32 is positioned within the retaining ring 16 and includes locking fingers 33 extending upward about the outer surface of the ball joint 20. The locking sleeve 32 may be in contact with the outer surface of the ball joint 20 such that the locking fingers 33 retain the ball joint 20 while permitting the ball joint 20 to move within the locking mechanism.

Referring now to FIGS. 3 and 3A, the lock 36 may be a lever including an engagement portion 37, a pivot 38, and a tab 39. The lock mount 35 secures the lock 36 to the ring portion 18. The engagement portion 37 is configured to contact the outer surface of the locking sleeve 32. The distal tip 37a of the engagement portion 37 may be contoured to conform to the shape of the outer surface of the locking sleeve 32. The pivot 38 is substantially aligned in a plane $C_p$ with the center of rotation $C_r$ of the ball joint 20.

Figure 4:
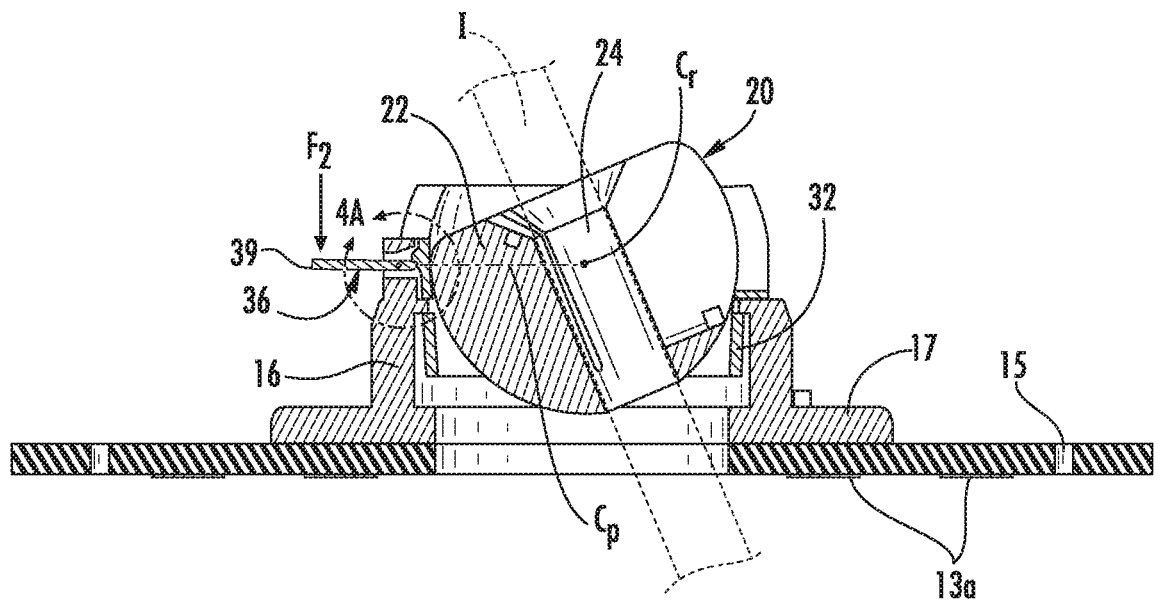
FIG. 4 is a side, cross-sectional view illustrating the locking mechanism of FIG. 3 in a first locked position and the channel in an unsecured configuration.
Figure 5:
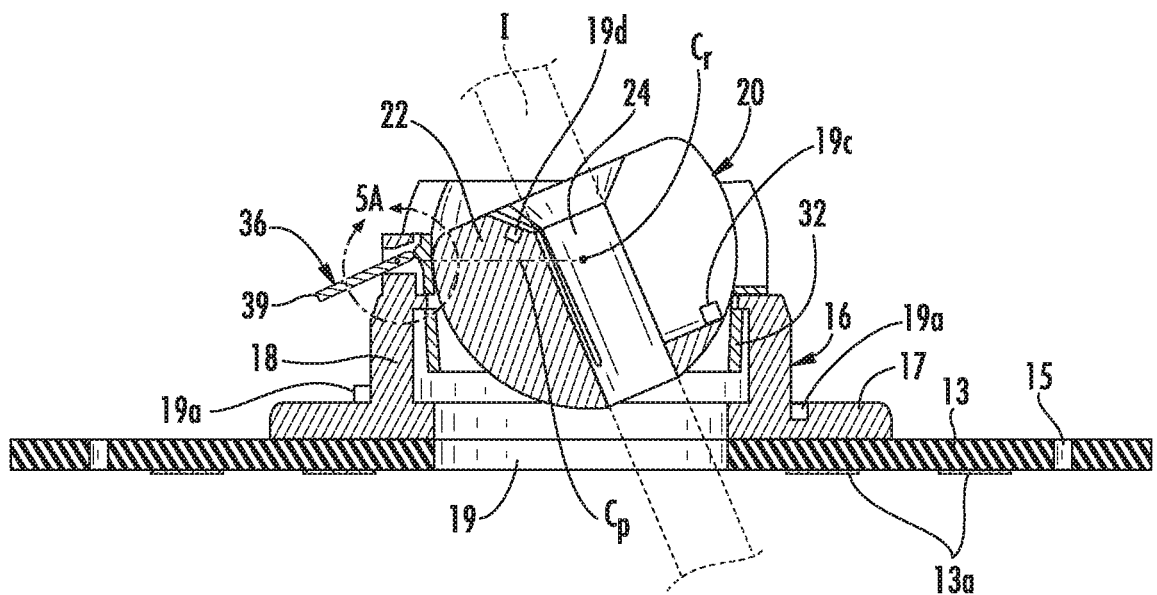
FIG. 5 is a side, cross-sectional view illustrating the locking mechanism of FIG. 3 in a second locked position and the channel in a secured configuration.

With reference to FIGS. 3-5A, the locking mechanism has an unlocked position (FIG. 3), a first locked position (FIG. 4), and a second locked position (FIG. 5). In the unlocked position of the locking mechanism 30, shown in FIGS. 3 and 3A, the ball joint 20 is movable within the locking sleeve 32 and the channel 24 is in an unsecured configuration such that a surgical instrument is insertable through the channel 24 (i.e., the surgical instrument "I" is free to slide or rotate within the channel 24). In the unlocked position, the locking sleeve 32 may partially frictionally interfere with the ball joint 20 such that the ball joint 20, and instrument "I" inserted therethrough, are retained in position relative to the retaining ring 16 until an external force is applied to the ball joint 20 or instrument "I" (e.g., the ball joint 20 resists environmental forces but is free to move within the retaining ring 16 in response to force applied by a clinician). The locking sleeve 32 may engage the engagement portion 37 to bias the locking mechanism 30 into the unlocked position when the lock 36 is between the unlocked position and the first locked position. As represented by arrow $F_1$ in FIG. 3, a clinician engages the tab 39 of the lock 36 to transition the locking mechanism 30 to the first locked position.

Figure 4A:
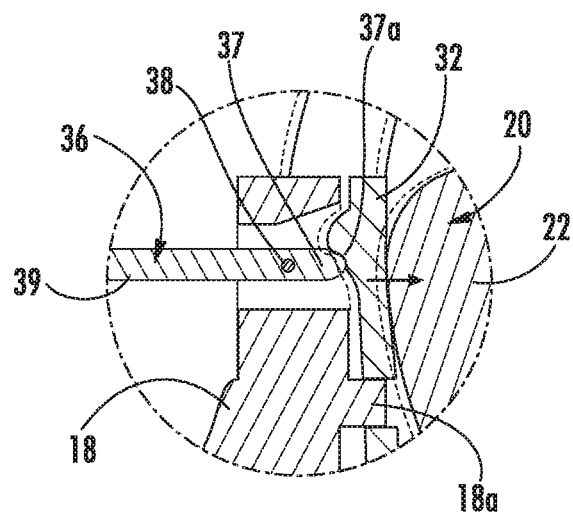
FIG. 4A is an enlarged view of the indicated area of detail of FIG. 4.

In the first locked position of the locking mechanism 30, shown in FIGS. 4 and 4A, the ball joint 20 is fixed relative to the locking sleeve 32 and the channel 24 is in the unsecured configuration. In the first locked position, the lock 36 may be substantially parallel to the base flange 17. The engagement portion 37 of the lock 36 engages the outer surface of the locking sleeve 32 such that the contour of the distal tip 37a matches the contour of the outer surface of the ball joint 20 to maintain the locking mechanism 30 in the first locked position. The engagement of the distal tip 37a with the locking sleeve 32 may provide indicia to a clinician (e.g., tactile feedback) that the locking mechanism 30 is in the first locked position.

As represented by arrow $F_2$ in FIG. 4, a clinician engages the tab 39 of the lock 36 to transition the locking mechanism 30 from the first locked position to the second locked position. In the second locked position of the locking mechanism 30, shown in FIGS. 5 and 5A, the ball joint 20 is fixed relative to the locking sleeve 32 and the channel 24 is in a secured configuration such that a surgical instrument "I" is fixed within the channel 24 (i.e., the surgical instrument "I" is prevented from sliding or rotating within the channel 24). The channel 24 of the ball joint 20 may be a deformable channel. In the second locked position, the locking sleeve 32 may urge the lobes 22 inward deforming the channel 24 to fix the surgical instrument "I" within the channel 24. The locking sleeve 32 may engage the engagement portion 37 to bias the locking mechanism 30 into the second locked position when the lock 36 is between the first locked position and the second locked position.

Figure 5A:
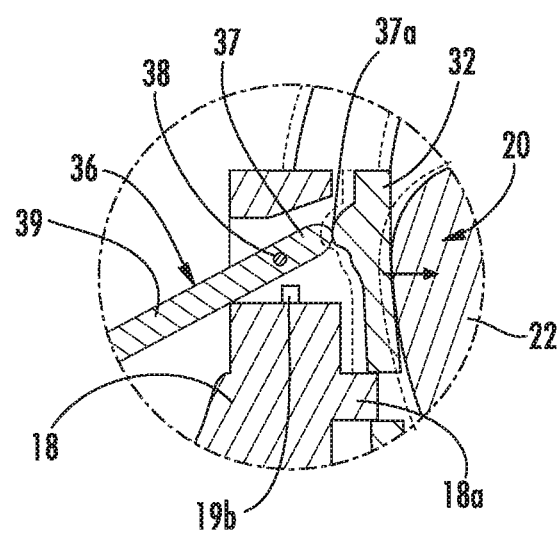
FIG. 5A is an enlarged view of the indicated area of detail of FIG. 5.

With particular reference to FIGS. 5 and 5A, the instrument fixation device 10 may include one or more sensors 19a-d to provide an indication of a position of or a condition of the instrument fixation device 10. A position sensor 19a may provide an indication of the position of the instrument fixation device 10 relative to the reference pad 108 (FIG. 1) or the sensors 106 (FIG. 1). The instrument fixation device 10 may include a plurality of position sensors 19a positioned on or within the instrument fixation device 10 (e.g., a sensor 19a may be associated with each wing 14, with the retaining ring 16, or with the ball joint 20). The tracking module 102 may determine the position or orientation of the instrument fixation device 10 from the positions of the plurality of position sensors 19a relative to the reference mat 108. In addition, the locking mechanism 30 may include a lock sensor 19b to provide an indication of the position of the locking mechanism 30 to the tracking module 102. Further, one or more angular sensors 19c may be associated with the ball joint 20 to provide an indication of the alignment of the channel 24 relative to the retaining ring 16. Moreover, an instrument sensor 19d may be operatively associated with the channel 24 to provide an indication of the presence of an instrument within the channel 24 (e.g., the instrument I) and/or the condition of the channel 24 (i.e., secured or unsecured). The instrument sensor 19d may also provide an indication of a length of an instrument extending through the channel 24 and into the surgical site. The instrument sensor 19d may detect reference points on an outer surface of an instrument inserted through the channel 24 or the instrument sensor 19d may have a roller (not shown) that engages the outer surface of an instrument inserted through the channel 24. It is within the scope of this disclosure that each of the sensors 19 provide an indication as detailed above with respect to sensors 19a-d.

The tracking module 102 may be configured to determine the position of a surgical instrument within the surgical site. For example, the tracking module 120 may receive an indication of the position of the instrument fixation device 10, the orientation of the instrument fixation device 10, the alignment of the channel 24 relative to the instrument fixation device 10, and the length of the instrument 120 extending from the channel 24 to determine the position of the surgical instrument 120 within the surgical site. The tracking module 102 may receive a signal from one or more of the sensors 19 providing an indication of a position of or a condition of the instrument fixation device 10. The tracking module 102 may receive a signal for one or more of the sensors 19a-d and the sensors 106 by a direct (i.e., wired connection) or a wireless connection. The wireless connection may be via radio frequency, optical, WIFI, Bluetooth®, creating personal area networks (PANs)), etc. It is within the scope of this disclosure that the instrument I may act as an antenna for the sensors 19a-d.

With reference to FIGS. 1-5A, the reference pad 108 is placed on a surgical table 110. The reference pad 108 may be integral to the surgical table 110. A patient is positioned on the surgical table 110 over the reference pad 108. The plurality of sensors 106 are positioned at reference points on the patient P. The plurality of sensors 106 provides an indication of the alignment of the patient P relative to the surgical table 110 to the tracking module 102. The tracking module 102 may align presurgical scans (e.g., X-rays, CT scans, MRIs, etc.) of the patient with the alignment of the patient P on the surgical table 110.

The instrument fixation device 10 is positioned and orientated about the surgical site of the patient P. The tracking module 102 or computer 104 may determine the surgical site from the alignment of the patient P on the surgical table 110 and from the presurgical scans. The tracking module 102 may receive a signal from one or more sensors 19a-d of the instrument fixation device 10 while the instrument fixation device 10 is positioned about the surgical site and provide an indication to the clinician when the instrument fixation device 10 is positioned and orientated about the surgical site. When the instrument fixation device 10 is positioned and orientated about the surgical site, a clinician secures the instrument fixation device 10 to the patient P as detailed above with the locking mechanism 30 of the instrument fixation device 10 in an unlocked position.

An instrument (e.g., instrument 120) is inserted through the channel 24 of the instrument fixation device 30. The channel 24 of the instrument fixation device 10 is aligned in a desired orientation relative to the surgical site. The desired orientation of the channel 24 may be predetermined from the presurgical scans. An indication of the alignment of the channel 24 with the surgical site is provided to the tracking module 102 by sensors 19a-d. The channel 24 may be aligned before or after the instrument is inserted through the channel. When the channel 24 is aligned before the instrument is inserted through the channel 24, the locking mechanism 30 is locked in the first locked position to fix the channel 24 relative to the surgical site before the instrument is inserted through the channel 24. When the channel 24 is aligned after the instrument is inserted through the channel 24, the instrument may be used to align the channel 24 before the locking mechanism 30 is locked in the first locked position. When locking mechanism 30 is in the first locked position with the instrument inserted through the channel 24, a length of the instrument is inserted through the channel 24 to a desired depth within the surgical site. The desired depth may be predetermined from the presurgical scans. An indication of the length of the instrument inserted through the channel 24 and into the surgical site is provided to the tracking module 102 by sensors 19a-d. When the instrument is at the desired depth within the surgical site, the locking mechanism 30 is locked in the second locking position to secure the instrument within the channel 24. The tracking module 102 or the computer 104 may provide an indication that the instrument is at the desired depth.

Figure 6:
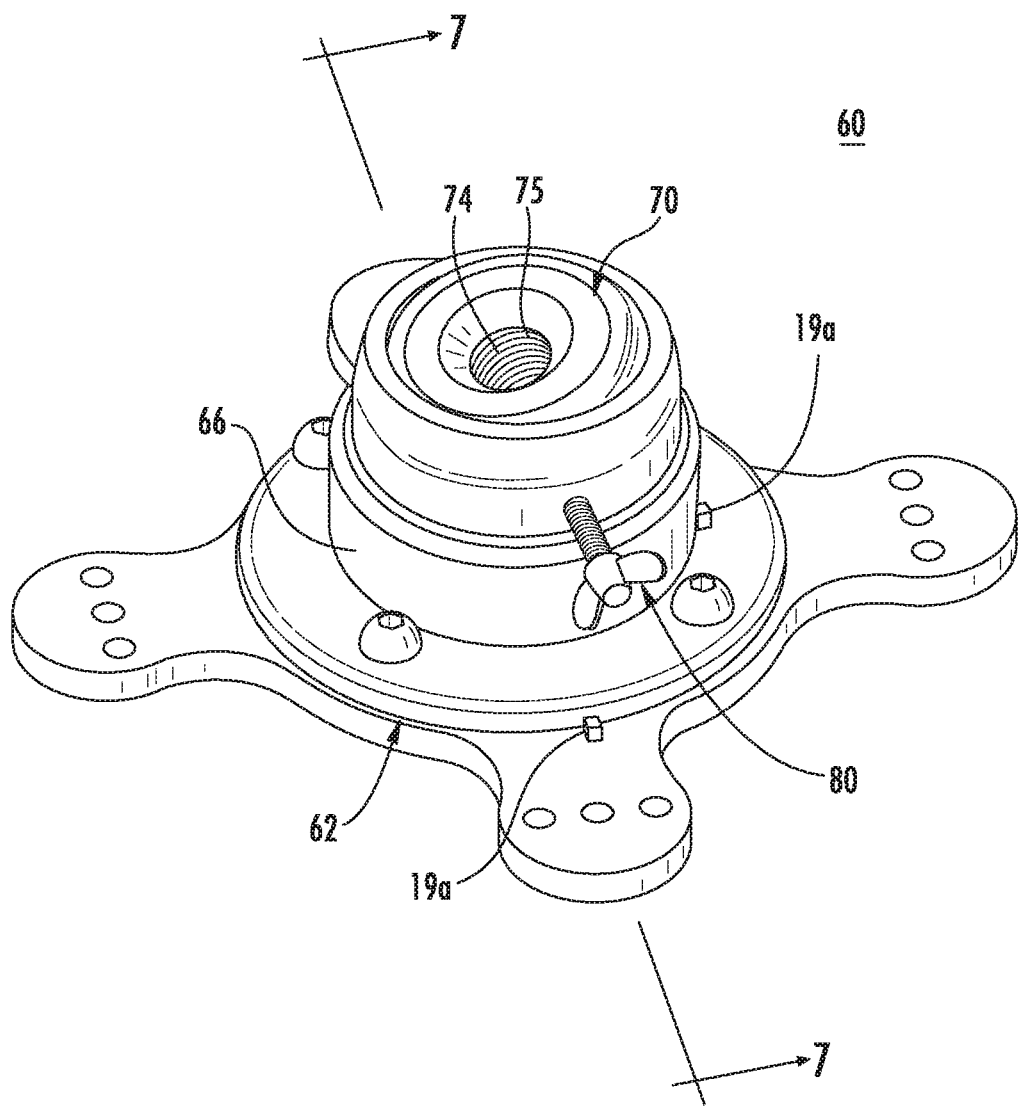
FIG. 6 is a perspective view of another illustrative embodiment of an instrument fixation device provided in accordance with the present disclosure including a base, a ball joint, and at locking mechanism in an first locked position.
Figure 7:
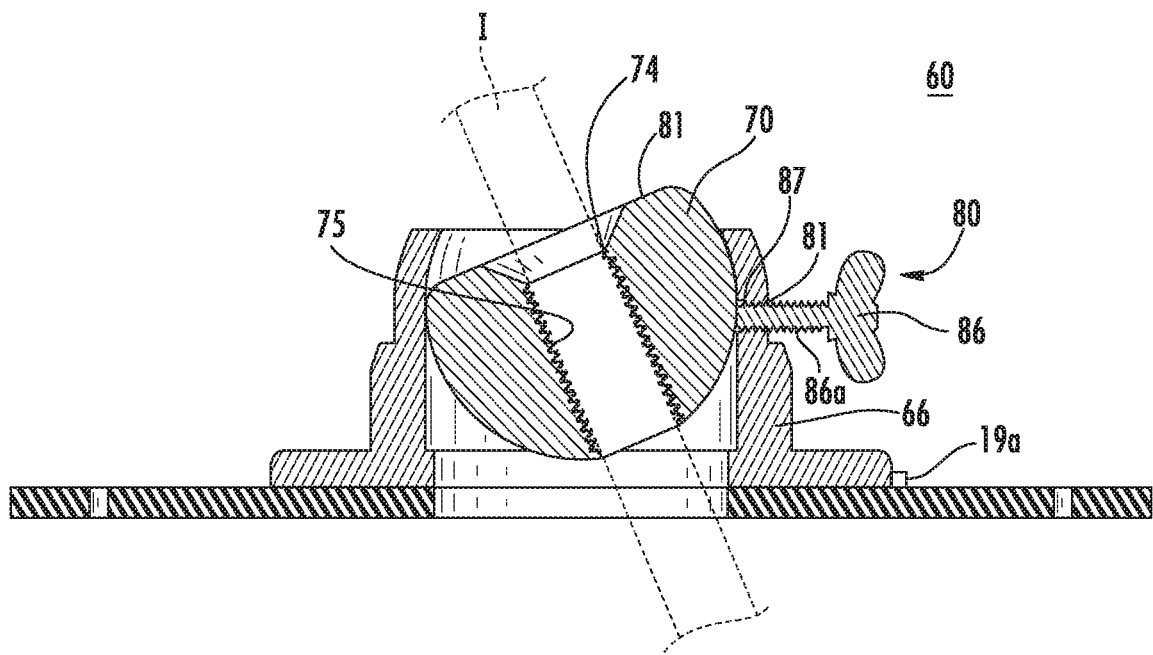
FIG. 7 is a side, cross-sectional view of taken along the line 7-7 of FIG. 6 illustrating the threaded channel of the instrument fixation device and the locking mechanism in a first locked position.

Referring to FIGS. 6 and 7, another instrument locking device 60 is provided in accordance with the present disclosure including a base 62, a ball joint 70, and a locking mechanism 80. The base 62, the ball joint 70, and the locking mechanism 80 are substantially similar to the base 12, the ball joint 20, and the locking mechanism 30 detailed above with respect to instrument locking device 10, as such only the differences will be detailed below for reasons of brevity. The instrument fixation device 60 may further include a plurality of sensors 19a-d as detailed above.

The base 62 includes a retaining ring 66 that defines a threaded hole 81. The ball joint 70 is substantially spherical in shape and may include a flattened upper surface 81. The ball joint defines a channel 74 includes threads 75 for threadably receive an instrument I (e.g., instrument 120). The length of the instrument I extending through the channel 74 may be determined and fixed by the cooperation of the threads 75 of the threaded channel 74 and threads of the instrument (not shown). The locking mechanism 80 includes a lock 86 in the form of a screw. The lock 86 includes threads 86a that cooperate with the threads of the threaded hole 81 such that an engagement portion 87 of the lock 86 is configured to fix the ball joint 70 relative to the retaining ring 66. The engagement portion 87 may directly engage the ball joint 70 or engage a locking sleeve 82 positioned about the ball joint 70.

In an unlocked position of the locking mechanism 80, the engagement portion 87 of the lock 86 is positioned such that the ball joint 70 is movable within the retaining ring 66. In a first locked position of the locking mechanism 80, the engagement portion 87 of the lock 86 engages the ball joint 70 to fix the ball joint relative to the retaining ring 66 as detailed above.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed:

1. An instrument fixation device comprising:
    a retaining ring having an inner surface;
    a ball joint having an outer surface and a channel defined therethrough, the ball joint movable within the retaining ring; and
    a locking mechanism including:
        a locking sleeve disposed between the inner surface of the retaining ring and the outer surface of the ball joint; and
        an engagement portion, the locking mechanism having an unlocked position in which the ball joint is free to move within the retaining ring a first locked position in which the engagement portion urges the locking sleeve into engagement with the outer surface of the ball joint to fix the ball joint relative to the retaining ring, and a second locked position in which the locking sleeve engages the outer surface of the ball joint to fix the ball joint relative to the retaining ring and deforms the channel.

2. The device according to claim 1, further comprising a position sensor configured to provide an indication of the location of the device relative to a surgical site.

3. The device according to claim 1, further comprising an angular sensor configured to provide an indication of the orientation of the ball joint relative to the retaining ring.

4. The device according to claim 1, further comprising a malleable pad fixed to a bottom surface of the retaining ring.

5. The device according to claim 4, wherein the malleable pad includes a plurality of wings extending radially away from the retaining ring, at least one of the plurality of wings defining a suture hole configured to receive a suture to secure the device to a patient.

6. The device according to claim 4, wherein the malleable pad has anti-microbial properties.

7. The device according to claim 4, wherein a bottom surface of the malleable pad includes an adhesive layer configured to secure the device to a patient.

8. The device according to claim 1, wherein the ball joint has an unsecured configuration in which the channel is configured to slidably and rotatably receive a surgical instrument and a secured configuration in which the channel is configured to fix a surgical instrument relative to the ball joint.

9. The device according to claim 8, wherein the ball joint includes two or more lobes, wherein in the unsecured configuration the channel is undeformed and in the secured configuration the channel is deformed.

10. The device according to claim 1, wherein the ball joint is movable in three degrees of freedom relative to the retaining ring.

11. The device according to claim 1, wherein the engagement portion is configured to provide tactile feedback to a clinician when the locking mechanism transitions from the unlocked position to the first locked position.

12. The device according to claim 1, wherein the engagement portion engages the locking sleeve to engage the locking sleeve with the ball joint.

13. A surgical navigation system comprising:
a surgical instrument; and
an instrument fixation device including:
  a retaining ring having an inner surface;
  a ball joint having an outer surface and a channel defined therethrough, the ball joint movable within the retaining ring, the surgical instrument received within the channel and extending into a surgical site; and
  a locking mechanism having:
    a locking sleeve disposed between the inner surface of the retaining ring and the outer surface of the ball joint; and
    an engagement portion, the locking mechanism having an unlocked position in which the ball joint is free to move within the retaining ring, a first locked position in which the engagement portion urges the locking sleeve into engagement with the outer surface of the ball joint to fix the ball joint relative to the retaining ring, and a second locked position in which the locking sleeve engages the outer surface of the ball joint to fix the ball joint relative to the retaining ring and deforms the channel to fix the surgical instrument relative to the ball joint.

14. The system according to claim 13, wherein the instrument fixation device includes an instrument sensor configured to provide an indication of a length of the surgical instrument extending through the channel and into a surgical site.

15. The system according to claim 14, wherein the surgical instrument includes a distal end portion extending from the channel into a surgical site, the instrument fixation device includes a position sensor configured to provide an indication of the position of the instrument fixation device, and wherein the system includes a tracking module configured to determine a length of the surgical instrument extending into a surgical site from the length of the instrument extending from the channel and the position of the instrument fixation device.

16. A method for positioning a surgical instrument within a surgical site, the method comprising:
securing an instrument fixation device to a patient over a surgical site, the instrument fixation device including:
  a retaining ring having an inner surface; and
  a ball joint having an outer surface and a channel defined therethrough, the ball joint movable within the retaining ring, the surgical instrument received within the channel and extending into a surgical site;
inserting a length of a surgical instrument through the channel of the instrument fixation device and into the surgical site;
locking the ball joint relative to the retaining ring with a locking sleeve disposed between the inner surface of the retaining ring and an outer surface of the ball joint by engaging the outer surface of the ball joint with the locking sleeve; and
causing the locking sleeve to bias the outer surface of the ball joint while the ball joint is locked relative to the retaining ring to deform the channel to fix the surgical instrument relative to the ball joint.

17. The method according to claim 16, wherein locking the ball joint relative to the retaining ring includes moving a lock to a first locked position.

18. The method according to claim 16, wherein causing the locking sleeve to bias the outer surface of the ball joint while the ball joint is locked relative to the retaining ring includes moving a lock to a second locked position.

19. The method according to claim 16, wherein causing the locking sleeve to bias the outer surface of the ball joint while the ball joint is locked relative to the retaining ring to deform the channel includes urging a plurality of lobes of the ball joint toward the channel.

* * * * *